United States Patent [19]
Matsutani et al.

[11] Patent Number: 5,143,269
[45] Date of Patent: Sep. 1, 1992

[54] MEDICAL STAPLER

[75] Inventors: Kanji Matsutani; Kimio Suzuki, both of Takanezawa; Masatoshi Fukuda, Utsunomiya; Katsutoshi Sato, Kamikawachi, all of Japan

[73] Assignee: Matsutani Seisakusho Co., Ltd., Japan

[21] Appl. No.: 824,105

[22] Filed: Jan. 22, 1992

[30] Foreign Application Priority Data

Feb. 12, 1991 [JP] Japan .................................. 3-38934

[51] Int. Cl.⁵ ............................................ A61B 17/068
[52] U.S. Cl. ...................................... 227/177; 227/19; 227/156; 227/175
[58] Field of Search ................. 227/175, 176, 177, 19, 227/156

[56] References Cited

U.S. PATENT DOCUMENTS

| | | | |
|---|---|---|---|
| 4,349,028 | 9/1982 | Green | 227/175 X |
| 4,411,378 | 10/1983 | Warman | 227/19 |
| 5,022,579 | 6/1991 | Matsutani et al. | 227/177 |
| 5,080,275 | 1/1992 | Meimerl et al. | 227/176 |

Primary Examiner—Frank T. Yost
Assistant Examiner—Rinaldi Rada
Attorney, Agent, or Firm—Wegner, Cantor Mueller & Player

[57] ABSTRACT

A medical stapler includes a front wall having an opening at a lower end portion thereof. A mirror is mounted in the vicinity of an upper edge of this opening. A straight line, representing a wound pinched by a pincette by the operator, is reflected on the mirror. The operator adjusts the posture of the stapler so that the straight line of the actual wound can be aligned with the straight line reflected on the mirror, and in this condition the staple is shaped so as to effect the suturing of the wound.

8 Claims, 5 Drawing Sheets

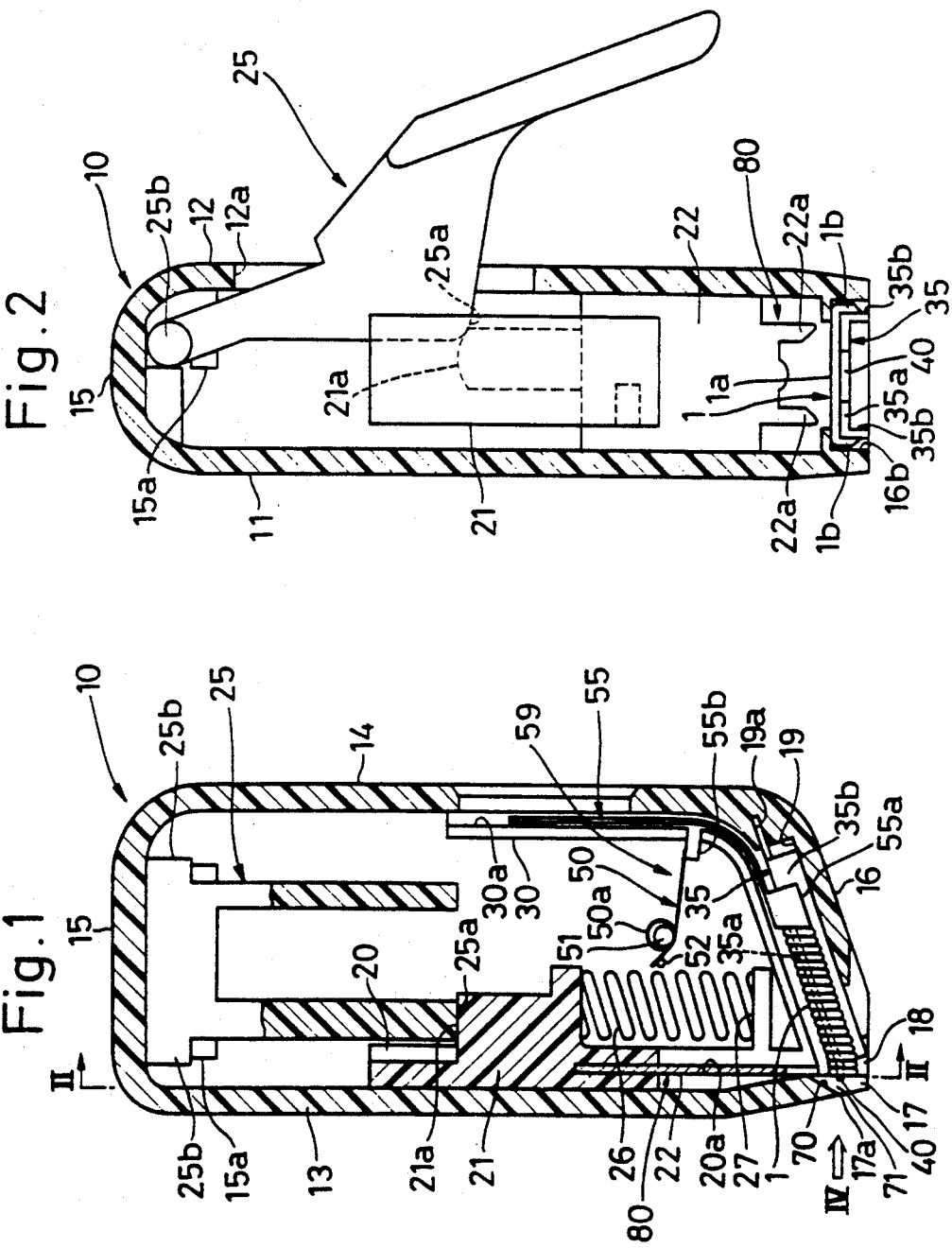

MEDICAL STAPLER

BACKGROUND OF THE INVENTION

This invention relates to a medical or surgical stapler.

A medical stapler disclosed in U.S. Pat. No. 4,411,378, includes a casing having a front wall. A ram is mounted within the casing so as to slidingly move along the front wall. An opening is formed in the lower end portion of the front wall. This opening is formed by an upper edge, disposed perpendicular to a path of movement of the ram, and a pair of side edges extending respectively from the opposite ends of this upper edge in parallel relation to the path of movement of the ram. An anvil is provided in the path of movement of the ram, and is disposed in the vicinity of the opening. The center of the upper edge of the opening is aligned with the center of the width of the anvil in the direction of the length of the upper edge of the opening. Mounted within the casing is a staple supply device which holds a plurality of staples in contiguous relation to one another, and supplies these staples sequentially to the anvil. Each staple has a crown portion, and a pair of legs extending angularly from the opposite ends of the crown portion, respectively. The crown portion of the foremost staple is placed on the upper surface of the anvil, with its center aligned with the center of the width of the anvil, and is disposed in parallel relation to the upper edge of the opening. Through the cooperation of the advancing ram with the anvil, the foremost staple is shaped in such a manner that the pair of legs are moved toward each other, thereby suturing a wound of a patient during this shaping operation.

The above suturing operation will now be described in detail. The operator grasps the stapler with one hand, and holds a pincette with the other hand, and the opposed sides of the wound are brought toward each other by the pincette to render the wound generally straight. Then, an operating member of the stapler is manipulated to advance the ram so as to shape the foremost staple in the above-mentioned manner, thereby effecting the suturing operation. In order to achieve a good suturing, it is required to shape the staple while keeping the staple perpendicular to the wound. To meet this requirement, the operator must overhang the patient so that his eyes can be disposed right above the wound, and in this condition the operator must shape the staple, while confirming that the upper edge of the opening of the stapler is kept perpendicular to the wound. Therefore, the operator is forced to take an unnatural posture.

SUMMARY OF THE INVENTION

It is an object of this invention to provide a medical stapler which enables the operator to carry out a good suturing operation without taking an unnatural posture.

According to the present invention, there is a medical stapler comprising:

(a) a casing including a front wall having an opening at a lower end portion thereof;

(b) staple supply means mounted within the casing so as to hold a plurality of staples in contiguous relation to one another, the staple supply means sequentially supplying the staples to a position near the opening, each of the staples having a crown portion and a pair of legs extending respectively from opposite ends of the crown portion, and the crown portion of a foremost one of the plurality of staples extending in substantially parallel relation to the front wall;

(c) shaping means mounted on the casing so as to shape the foremost staple, disposed near the opening, in such a manner the pair of legs of the foremost staple are brought toward each other; and (d) a mirror mounted on an outer surface of the front wall in the vicinity of an upper edge of the opening.

BRIEF DESCRIPTION OF THE DRAWINGS

FIG. 1 is a vertical cross-sectional view of a medical stapler provided in accordance with the present invention;

FIG. 2 is a cross-sectional view taken along the line II—II of FIG. 1;

DESCRIPTION OF THE PREFERRED EMBODIMENT

Figure 4:
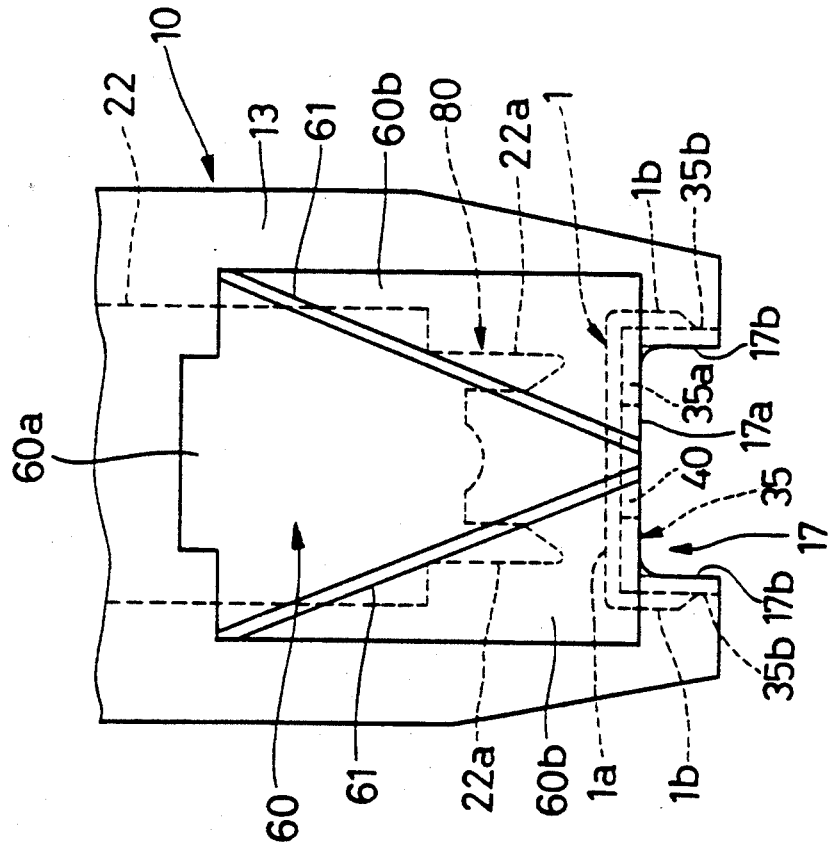
FIG. 4 is an enlarged front-elevational view of a lower end portion of a front wall of the stapler, as viewed in a direction IV of FIG. 1.

A preferred embodiment of the present invention will now be described with reference to the drawings. FIGS. 1 and 2 show a disposable stapler. This stapler comprises an elongate hollow casing 10 made of a resin. The casing 10 has a pair of opposed flat side walls 11 and 12 extending longitudinally in generally parallel relation to each other, and also has a front wall 13, a rear wall 14, an upper wall 15 and a lower wall 16 which perpendicularly intersect the side walls 11 and 12. The front wall 13 and the rear wall 14 extend longitudinally of the casing 10 in generally parallel relation to each other. The lower wall 16 is inclined with respect to the longitudinal axis of the casing 10. An opening 17 is formed at the lower end portion of the front wall 13. As shown in FIG. 4, this opening 17 has a rectangular shape, and is formed by an upper edge 17a (which is disposed perpendicular to a path of movement of a ram 22 (later described)), and a pair of side edges 17b extending downwardly respectively from the opposite ends of the upper edge 17a in parallel relation to the path of movement of the ram 22. An opening 18 continuous with the opening 17 is also formed at one end portion of the lower wall 16 close to the front wall 13.

A pair of parallel spaced guide portions 20 are formed integrally on the inner surface of the front wall 13, and extend longitudinally of the casing 10. In FIG. 1, only one of the two guide portions 20 is shown. A slider 21 is received between the pair of guide portions 20 for sliding movement therealong. The ram 22 made of a metal plate is fixedly secured at its upper end portion to the lower end portion of the slider 21. The ram 22 is slidably received in grooves 20a, formed respectively in the opposed surfaces of the guide portions 20. As shown in FIGS. 2 and 4, the ram 22 has a pair of downwardly-extending projections 22a formed at its lower end.

As shown in FIGS. 1 and 2, a bearing 15a is formed on the casing 10 adjacent to the upper end thereof, and a shaft portion 25b of an operating lever (operating member) 25 which is formed at the proximal end of this lever is pivotally supported by the bearing 15a. The operating lever 25 is extended outwardly from the casing 10 through an opening 12a formed through the side wall 12. A cam surface 25a is formed on the operating lever 25. When the operating lever 25 is pivotally moved toward the casing 10, the cam surface 25a urges a cam follower 21a, formed integrally with the slider 21, to move the slider 21 downward, thereby moving the ram 22 downward.

The slider 21 is urged upward by a return spring 26, so that the cam follower 21a is always held against the cam surface 25a of the operating lever 25. The return spring 26 acts between the slider 21 and a spring seat 27 formed integrally with the casing 10.

As shown in FIG. 1, a pair of projections 30 (only one of which is shown in FIG. 1) are formed integrally on the inner surfaces of the side walls 11 and 12 of the casing 10. More specifically, the pair of projections 30 extend from a point generally midway between the opposite ends of the rear wall 14 to the end of the lower wall 16 remote from the rear wall 14. Grooves 30a are formed respectively in the opposed surfaces of those portions of the projections 30 extending along the rear wall 14. A recess 19 is formed in the inner surface 16b of the lower wall 16 of the casing 10, and extends along the lower wall 16. One end of the recess 19 is continuous with the grooves 30a, and the other end thereof is continuous with the openings 17 and 18 of the casing 10.

Figure 5:
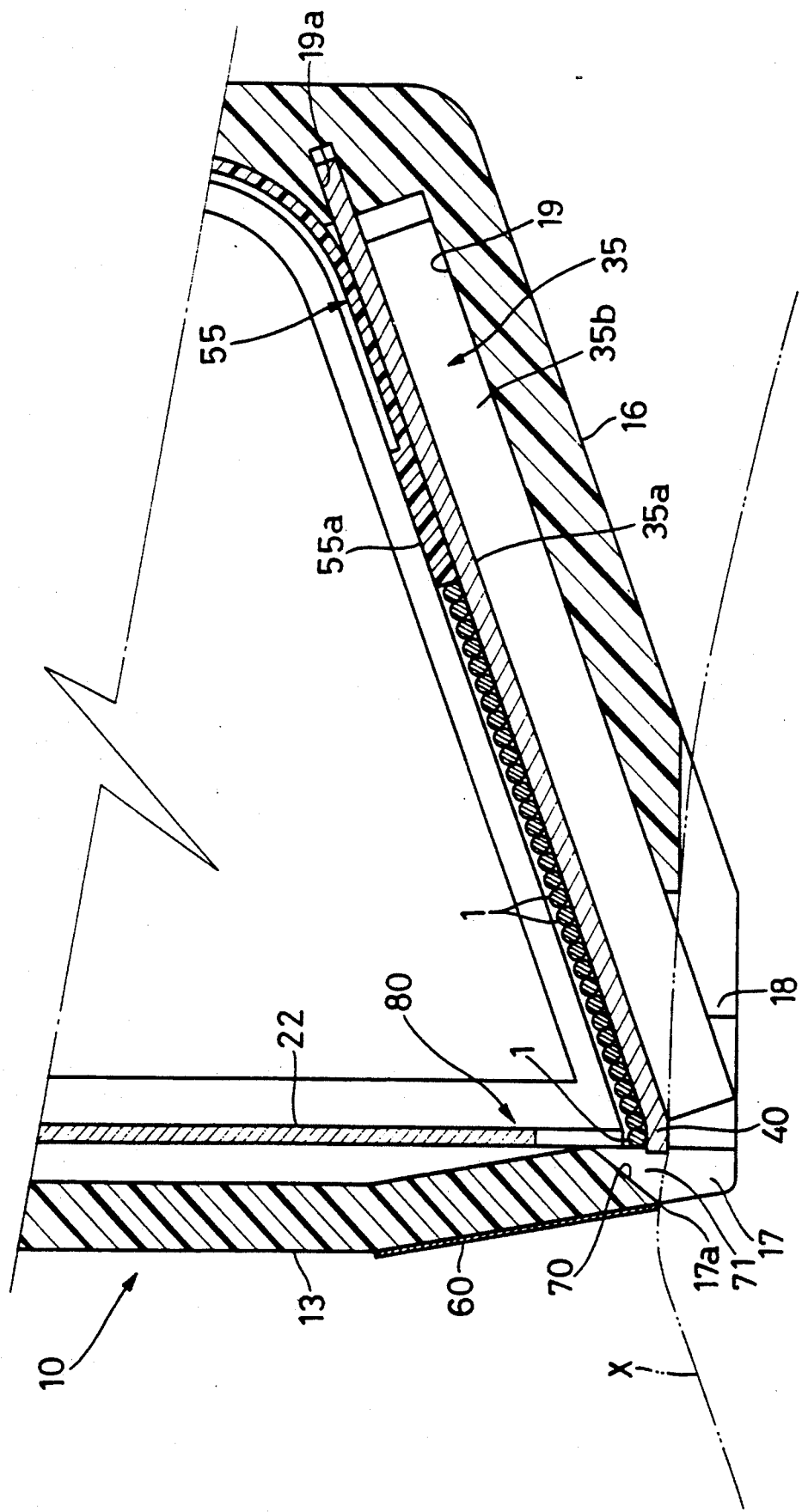
FIG. 5 is an enlarged cross-sectional view of a lower end portion of the stapler.

A guide member 35 made of a metal plate is fixedly received in the recess 19. The guide member 35 extends along the lower wall 16, that is, in a direction intersecting the path of movement of the ram 22. As shown in FIGS. 4 and 5, the guide member 35 has a flat base plate portion 35a, and a pair of side plate portions 35b formed respectively at the lateral edges of the base plate portion 35a. The rear end portion of the base plate portion 35a is received in a groove 19a formed in a rear side wall of the recess 19.

An anvil 40 is formed integrally with and extends from the front end of the base plate portion 35a of the guide member 35 toward the opening 17. The anvil 40 is disposed in the path of movement of the ram 22. The upper and lower surfaces of the anvil 40 are disposed generally perpendicular to the path of movement of the ram 22. The distance between the pair of projections 22a is larger than the width of the anvil 40 by an amount slightly larger than the double of the diameter of a crown portion 1a of the staple 1. The operating member 25, the ram 22 and the anvil 40 jointly constitute a shaping means 80.

A number of staples 1 are supported on the guide member 35, and are arranged in contiguous relation to one another in the direction of the length of the guide member 35. Each staple 1 is formed by pressing a stainless steel wire of a circular cross-section having a predetermined length and a diameter of about 0.5 mm. As best shown in FIGS. 2 and 4, the staple 1 has the straight crown portion 1a, and a pair of legs 1b extending perpendicularly from the opposite ends of the crown portion 1a, respectively. The distal end of each leg 1b is cut obliquely to provide a piercing ability. Each staple 1 is supported on the guide member 35 in straddling relation thereto. More specifically, the crown portion 1a of the staple 1 is borne by the base plate portion 35a of the guide member 35, and the pair of legs 1b are disposed outwardly of the pair of side plate portions 35b of the guide member 35 in slightly spaced, opposed relation thereto.

As shown in FIG. 1, a number of staples 1 are urged by a spring 50 via a push member 55. More specifically, the push member 55 comprises an elongate plate so flexible as to be bent. The lateral edges of the push member 55 are slidably received respectively in the grooves 30a of the projections 30. An abutment portion 55a of an inverted U-shaped cross-section is formed at the distal end of the push member 55, and this abutment portion 55a is slidably supported on the guide member 35 in straddling relation thereto. A projection 55b is formed on the push member 55 intermediate the opposite ends thereof. The spring 50 has a coiled portion 50a which is supported on a projection 51 formed on the casing 10. One end of the spring 50 is retained by a projection 52 formed on the casing 10, and the other end of the spring 50 is firmly held against the projection 55b of the push member 55 under the resilient force of the spring 50, thereby urging the push member 55 downward. Therefore, the abutment portion 55a of the push member 55 is firmly abutted against the rearmost staple 1 to urge a number of staples 1 toward the anvil 40. The guide member 35, the spring 50 and the push member 55 jointly constitute a staple supply mechanism 59.

The foremost staple 1 is retained by the inner surface of the front wall 13 in the vicinity of the side edges 17b of the opening 17, and its crown portion 1a is placed on the anvil 40. The crown portion 1a is disposed parallel to the front wall 13 and the upper edge 17a of the opening 17. As shown in FIG. 4, the center of the crown portion 1a, the center of the anvil 40 and the center of the upper edge 17a of the opening 17 are aligned with one another in the direction of the length of the crown portion 1a.

Figure 3:
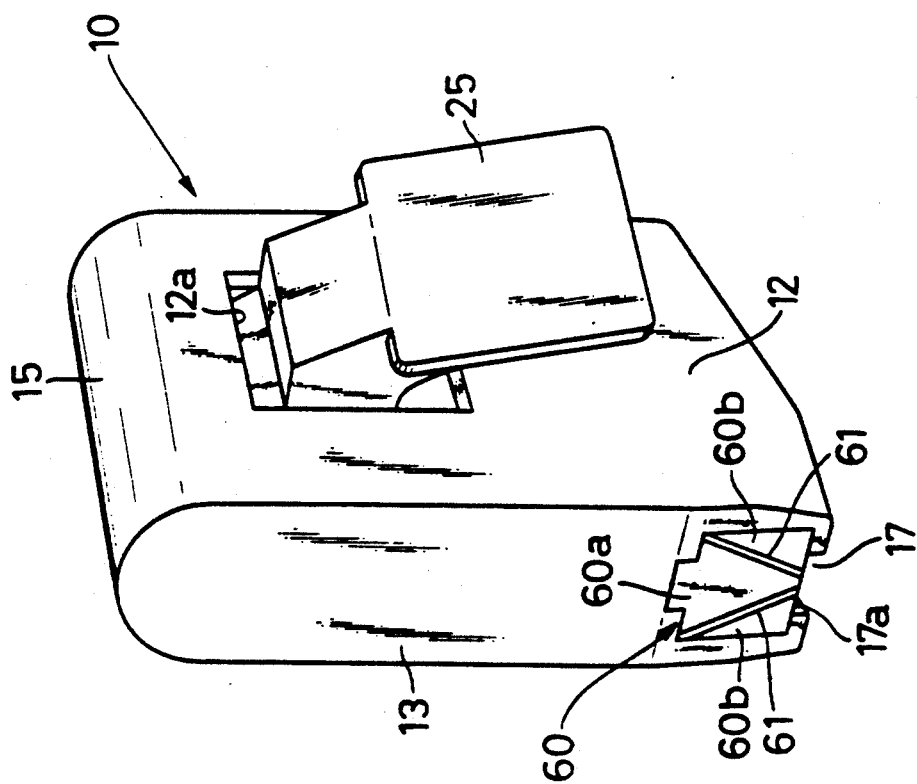
FIG. 3 is a perspective view of the stapler.

Next, important features of the present invention will now be described. As shown in FIGS. 3 and 4, a mirror 60 of a generally rectangular shape is mounted on the outer surface of the front wall 13 in the vicinity of the upper edge 17a of the opening 17. The mirror 60 extends upwardly a predetermined distance from the upper edge 17a. For example, the mirror 60 comprises a paper sheet having a metal film bonded to an outer surface thereof, and the mirror 60 is bonded to the front wall 13. The mirror 60 may comprise a film or a plate of metal (e.g. stainless steel, aluminum or the like) having a polished surface. As another alternative, the mirror 60 may be formed by vapor-depositing aluminum or the like on the front wall 13. A pair of straight lines 61 are depicted or printed on the mirror 60 by printing ink, and are disposed symmetrically with respect to the longitudinal axis of the mirror 60. The pair of straight lines 61 are inclined with respect to the longitudinal axis of the casing 10, and approach toward each other progressively toward their lower ends. The pair of straight lines 61 extend downwardly to the upper edge 17a of the opening 17, with their lower ends closely spaced from each other. The center of the upper edge 17a is disposed at the narrow spacing between the lower ends of the two straight lines 61. In other words, the mirror 60 has a first reflection portion 60a of an isosceles triangular shape, and a pair of second reflection portions 60b of a right-angled triangular shape disposed respectively on the opposite sides of the first reflection portion 60a. The distal end of the first reflection portion 60a is disposed at a position aligned with the center of the upper edge 17a of the opening 17, the center of the anvil 40 and the center of the crown portion 1a of the staple 1.

The upper edge 17a of the opening 17 is disposed lower as compared with conventional staplers. Namely, as shown in FIG. 5, the upper edge 17a of the opening 17 is disposed between the plane of the upper surface of the anvil 40 and the plane of the lower surface of the anvil 40. The inner surface of that portion of the front wall 13 disposed above and immediately adjacent to the upper edge 17a of the opening 17 serves as an impingement surface 70 for the staple 1. The impingement surface 70 is disposed closer to the mirror 60 than the inner surface of the front wall 13 in the vicinity of the side edges 17b is. The impingement surface 70 is inclined downwardly away from the distal end of the anvil 40. A gap 71 is formed between the impingement surface 70 and the distal end of the anvil 40, and this gap 71 has a size greater than the diameter of the crown portion 1a of the staple 1, and allows the shaped staple 1 to pass therethrough as later described.

In the medical stapler of the above construction, when the ram 22 is moved downward by manipulating the operating member 25, the projections 22a of the ram 22 are brought into engagement with the crown portion 1a of the foremost staple 1. When the ram 22 further moves downward, the opposite end portions of the crown portion 1a are bent generally perpendicularly to the central portion thereof through the cooperation of the projections 22a with the anvil 40. During the process of bending the crown portion 1a in this manner, the distal ends of the pair of legs 1b are moved toward each other, so that they pierce into that portion of the patient to be sutured, and at the time when the shaping (bending) of the foremost staple 1 is completed, the staple 1 has a generally rectangular shape. By doing so, the suturing of that portion of the patient is completed. At the time when the shaping of the foremost staple 1 is finished, the legs 1b have been disengaged from the inner surface of the front wall 13 in the vicinity of the side edges 17b of the opening 17. Therefore, then, when the ram 22 is moved upward, the shaped staple is urged by the crown portions 1a of the subsequent staples, and is disengaged from the anvil 40 to be located at the gap 71. Thereafter, when moving the stapler upward, the shaped stapler attached to a wound portion is disengaged from the stapler.

Figure 6:
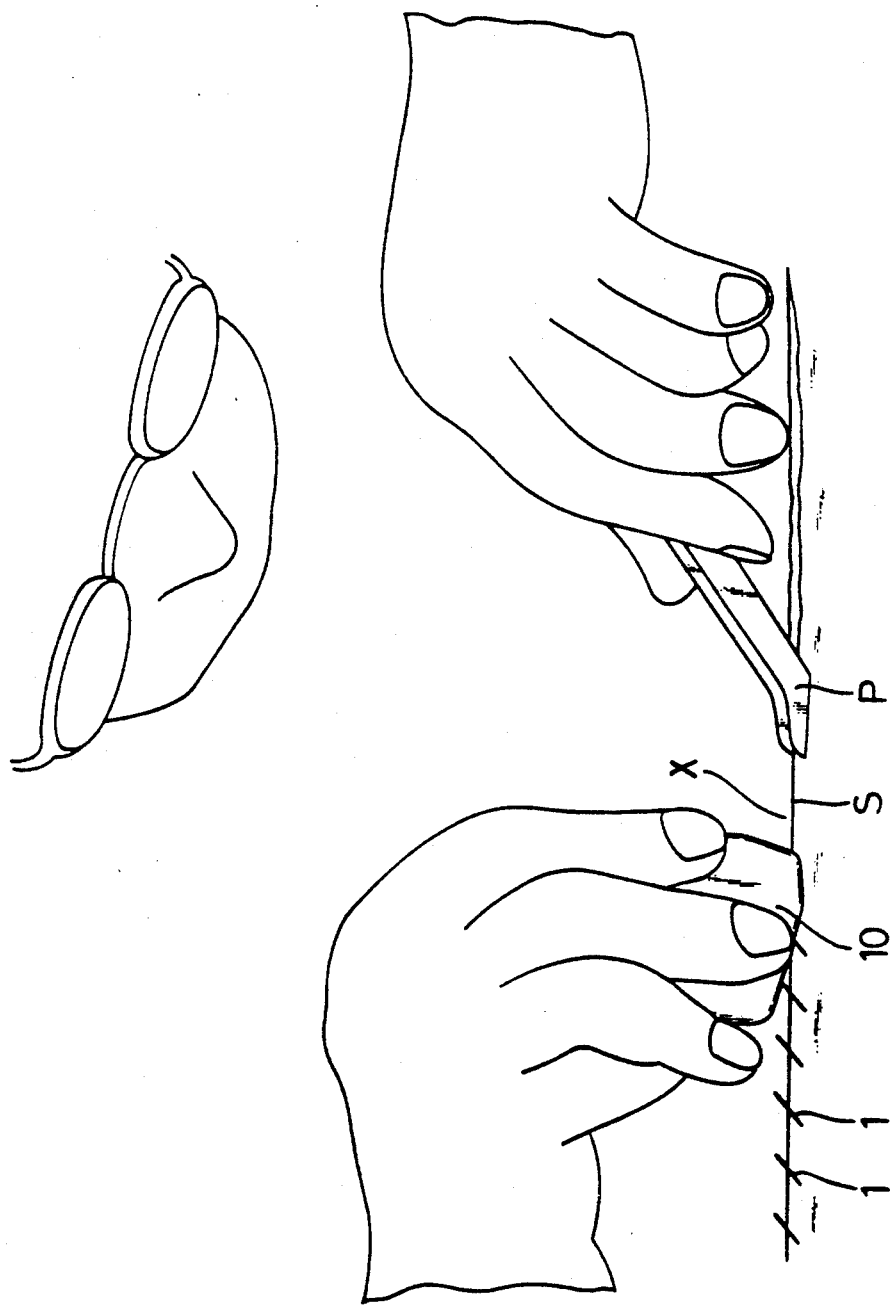
FIG. 6 is a view showing a condition in which a wound is being sutured using the stapler.
Figure 7:
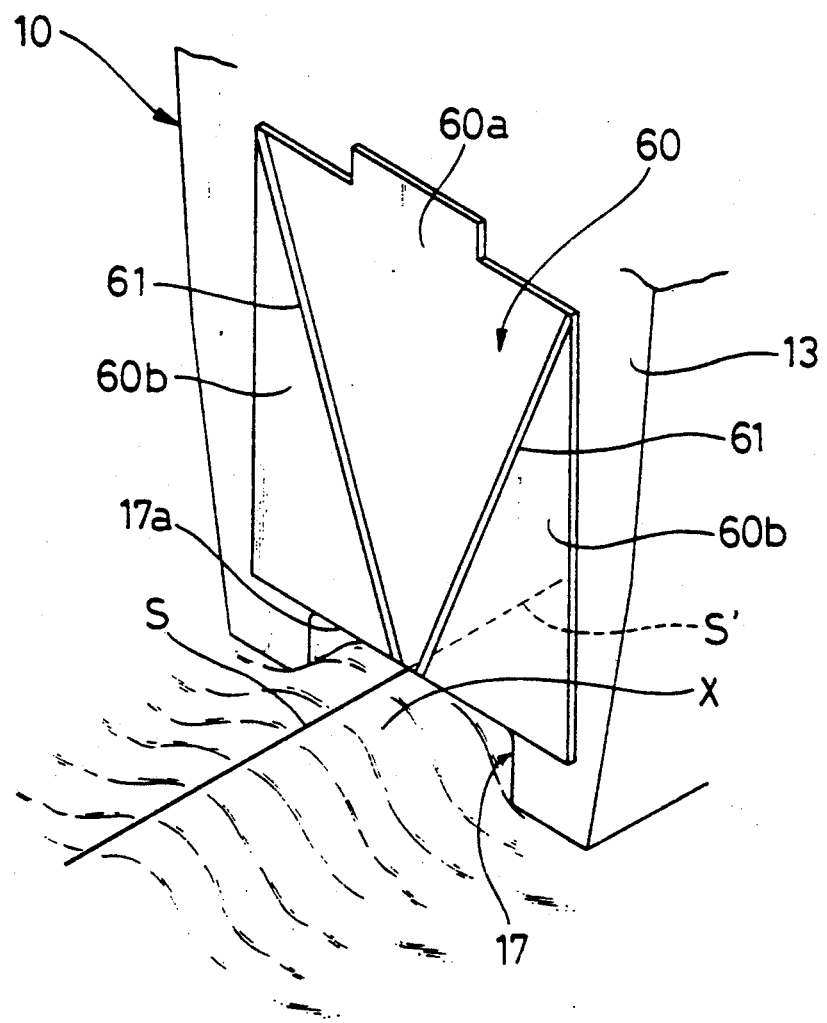
FIG. 7 is a perspective view of the wound and a mirror, as seen from the operator side.

Next, the suturing operation will now be described in detail with reference to FIGS. 5 to 7. As shown in FIG. 6, the operator grasps the casing 10 of the stapler with one hand, and holds a pincette P with the other hand, and the opposed sides of a wound S in the skin are brought toward each other by the pincette to render the wound S generally straight. Thus, the opposed sides of the wound S are pinched together by the pincette P, and are raised as at X. The stapler is so positioned that this raised portion X can be introduced into the openings 17 and 18, as shown in FIGS. 5 and 7. Then, the front wall 13 of the stapler is kept in a vertical condition, and in this condition the stapler is angularly moved about a vertical axis so as to adjust the position of the stapler so that the wound S can be aligned with a wound S' reflected in the mirror 60 (in which case the actual wound S and the reflected wound S' jointly constitute a common straight line), as shown in FIG. 7. As a result, the crown portion 1a of the foremost staple 1 is disposed perpendicular to the straight wound S. Here, it is important to note that in the condition in which the crown portion 1a of the foremost staple 1 is disposed perpendicular to the wound S (and hence the mirror 60 is disposed perpendicular to the wound S), the actual wound S is always aligned with the wound S' reflected on the mirror 60 regardless of the position of the eyes of the operator. Therefore, the operator does not need to overhang the patient so as to position his eyes right above the wound S, and hence the operator is not required to take an unnatural posture. Instead, the operator, while viewing the wound S obliquely from above this wound, can confirm that the wound S is disposed perpendicularly to the staple 1.

Since the upper edge 17a of the opening 17 is disposed between the plane of the lower surface of the anvil 40 and the plane of the upper surface of the anvil 40, the raised portion X urged by the lower surface of the anvil 40 can be brought into contact with the upper edge 17a of the opening 17. Therefore, by adjusting the position of the stapler so that the center of the upper edge 17a indicated by the distal end of the first reflection portion 60a can be in registry with the wound S, the center of the crown portion 1a of the foremost staple 1 can be brought into registry with the wound S. The operator can make this confirmation, while viewing the wound S obliquely from above this wound.

Thus, the position of the stapler is adjusted in the above manner, so that the foremost staple 1 is disposed perpendicular to the wound S, with the center of the crown portion 1a disposed in registry with the wound S, and in this condition the shaping of the staple 1 is effected, so that a good suturing can be done.

When the operator, before starting the suturing, operates the stapler for trial purposes to shape the foremost staple 1 without suturing the wound by this shaped staple 1, the shaped staple 1 is pushed by the subsequent staples 1 to vigorously jump from the anvil 40. In this case, however, since the upper edge 17a of the opening 17 is disposed at a level below the upper surface of the anvil 40, the shaped staple impinges on the inclined impingement surface 70, and drops downwardly. Thus, the shaped staple 1 will not jump forwardly, and will not become missing, and therefore this staple can be easily found.

Consideration is now given to the height of the upper edge 17a of the opening 17. Preferably, the upper edge 17a should be disposed between a position, which is higher than the plane of the upper surface of the anvil 40 by an amount corresponding to the diameter of the crown portion 1a of the staple 1, and the plane of the lower surface of the anvil 40. If the upper edge 17a is disposed at a position higher than the plane of the upper surface of the anvil 40 by an amount exceeding the diameter of the crown portion 1a, the gap between the raised portion X (against which the lower surface of the anvil 40 is held) and the upper edge 17a is large, which results in a possibility that it takes more time to confirm whether or not the center of the upper edge 17a is in registry with the wound S. Also, if the upper edge 17a is disposed at a level below the plane of the lower surface of the anvil 40, the upper edge 17a urges the raised portion X, so that a gap may be formed between the lower surface of the anvil 40 and the raised portion X. In order to more positively prevent the forward jumping of the staple 1 shaped for trial purposes, the upper edge 17a should preferably be disposed in registry with the plane of the upper surface of the anvil 40, or be disposed below this plane.

The present invention is not limited to the above embodiment, and various modifications can be made. For example, the anvil may be separate from the guide member. The mirror may be formed over the generally entire area of the front wall of the casing. The means for indicating the center of the upper edge of the opening may be a single line extending upwardly from the center of the upper edge of the opening along the path of movement of the ram. A plurality of mirrors may be mounted on the front wall of the casing, and the center of the upper edge of the opening may be indicated by the gap between these mirrors. The crown portion of the staple does not need to be straight, and may be curved into a generally M-shape.

What is claimed is:

1. A medical stapler comprising:
   (a) a casing including a front wall having an opening at a lower end portion thereof;
   (b) staple supply means mounted within said casing so as to hold a plurality of staples in contiguous relation to one another, said staple supply means sequentially supplying said staples to a position near said opening, each of said staples having a crown portion and a pair of legs extending respectively from opposite ends of said crown portion, and said crown portion of a foremost one of said plurality of staples extending in substantially parallel relation to said front wall;
   (c) shaping means mounted on said casing so as to shape the foremost staple, disposed near said opening, in such a manner said pair of legs of said foremost staple are brought toward each other; and
   (d) a mirror mounted on an outer surface of said front wall in the vicinity of an upper edge of said opening.

2. A medical stapler according to claim 1, in which said upper edge of said opening is disposed in substantially parallel relation to the crown portion of the foremost staple, the center of the crown portion of the foremost staple being substantially aligned with the center of said upper edge of said opening in a direction of the length of said crown portion of said foremost staple.

3. A medical stapler according to claim 2, in which said mirror extends upwardly from said upper edge of said opening.

4. A medical stapler according to claim 3, in which indication means for indicating the center of said upper edge of said opening is provided on said mirror.

5. A medical stapler according to claim 1, in which said shaping means comprises a ram mounted within said casing for sliding movement along said front wall, an operating member mounted on said casing for moving said ram downward, and an anvil disposed in a path of movement of said ram in the vicinity of said opening of said front wall, the crown portion of the foremost staple being placed on said anvil, and the foremost staple being shaped through the cooperation of the advancing ram with said anvil in such a manner that the pair of legs of said foremost staple are brought toward each other.

6. A medical stapler according to claim 5, in which said upper edge of said opening is disposed between a position, which is higher than the plane of an upper surface of said anvil by an amount corresponding to the diameter of said crown portion of said staple, and the plane of a lower surface of said anvil.

7. A medical stapler according to claim 6, in which said upper edge of said opening is disposed between the plane of the upper surface of said anvil and the plane of the lower surface of said anvil.

8. A medical stapler according to claim 7, in which said staple supply means comprises guide means for supporting said plurality of staples in contiguous relation to one another, and urging means for urging said plurality of staples, supported on said guide means, toward said anvil, said guide means extending in a direction intersecting the path of movement of said ram, before the shaping of the foremost staple, the pair of legs of the foremost staple being retained by an inner surface of said front wall in the vicinity of opposed side edges of said opening, an inner surface of that portion of said front wall disposed above and immediately adjacent to said upper edge of said opening serves as an impingement surface for the foremost staple, said impingement surface being disposed closer to said mirror than said inner surface of said front wall in the vicinity of the side edges of said opening is, so that a gap for allowing the crown portion of the shaped staple to pass therethrough is formed between said impingement surface and a distal end of said anvil, and said impingement surface being inclined downwardly away from the distal end of the anvil.

* * * * *